United States Patent [19]

Ward et al.

[11] 4,185,097
[45] Jan. 22, 1980

[54] METHOD OF COMBATING HERPES SIMPLEX VIRUSES WITH LIGNOSULFONATES

[75] Inventors: John W. Ward; Robert W. Tankersley, Jr., both of Richmond, Va.

[73] Assignee: A. H. Robins Company, Inc., Richmond, Va.

[21] Appl. No.: 868,010

[22] Filed: Jan. 9, 1978

[51] Int. Cl.² .................... A61K 35/78; A61K 31/185
[52] U.S. Cl. ..................................... 424/195; 424/315
[58] Field of Search ................................ 424/315, 195

[56] References Cited

U.S. PATENT DOCUMENTS 3,914,433 10/1975 Ward et al. .......................... 424/315

Primary Examiner—Jerome D. Goldberg

[57] ABSTRACT

A method is disclosed for combating Herpes simplex viruses, Types I and II, which comprises topically applying an antiviral lignosulfonate to the animal tissue under attack.

1 Claim, No Drawings

METHOD OF COMBATING HERPES SIMPLEX VIRUSES WITH LIGNOSULFONATES

BACKGROUND OF THE INVENTION

1. FIELD OF INVENTION

The present invention is concerned with the use of lignosulfonates to combat Herpes viruses and is particularly concerned with a novel method for treating infections caused by Types I and II Herpes simplex viruses in a living animal body using the lignosulfonates as antiviral agents.

Usually Herpes simplex viral infections are mild, acute or recurrent episodes with topical lesion resulting which causes pain and temporary cosmetic disfigurement during which time the host is potentially infectious to others. More rarely, the infection takes the form of a serious corneal, encephalitic or systemic disease. Type I Herpes simplex viral infections generally are associated with the oral cavity and Type II Herpes simplex viruses generally occur in the genitourinary tract of both sexes in humans; however, there is some cross-over of infection.

2. DESCRIPTION OF THE PRIOR ART

No specific anti-herpes agents are available for use in a host having the usual mild, acute or recurrent episode despite the obvious need for such agents. A wide range of non-specific treatments have some palliative and antiseptic effect such as alum, vinegar, ether, camphor and mixed culture of Lactobacillus acidophilus and L. bulgaricus with naturally occurring metabolic products produced by these organisms.

For more serious corneal, encephalitic and systemic infections, two specific anti-herpes agents are available: 5-iodo-2'-deoxyuridine and 9-D-arabinofuranosyl adenine. However, because the mechanism of control of virus with these agents involves interference with DNA synthesis, potential side effects detrimental to other DNA syntheses vital to the host also occurs.

Another approach to the therapy of Herpes simplex viral infections has been the use of photo-inactivating dyes. This procedure requires that the surface of the lesion be broken, the underlying infected tissue painted with a dye such as neutral red or proflavine and the painted area exposed to visible light of sufficient intensity to inactivate the stained virus. The efficacy and safety of the procedure using photoinactivating dyes have not been established and special equipment and trained personnel are required to administer the treatment.

Lignosulfonates have been shown to reduce gastric ulceration in rats caused by pyloric ligation. Vocac, J. A. and Alphin, R. S., Arch. Int. Pharmacodyn. 177 No. 1, pp 150–158. Lignosulfonates have also been used as a gargle to alleviate pain and discomfort associated with pharyngitis, U.S. Pat. No. 3,914,433.

SUMMARY OF THE INVENTION

The present invention is based on the discovery that topical application of an antiviral lignosulfonate to the affected area of a host mammal infected with Type I or Type II Herpes simplex viruses controls the virus and reduces the extent of infection. The method may also be used to combat infection prior to exposure. The preferred lignosulfonates are those having the higher molecular weights which are concentrated or separated by dialysis or reverse osmosis of solutions of lignosulfonates.

Lignosulfonates useful in the method of this invention are derived from sulfonation of naturally occurring lignins and any pharmaceutically acceptable cation may be employed.

Accordingly, it is an object of the present invention to provide a method for treating viral infections caused by Types I and II Herpes simplex viruses.

A further object of the present invention is to provide a method of treating Types I and II Herpes simplex viruses in mammals by topically administering an effective amount of an antiviral lignosulfonate to the tissue under attack.

A further object of the present invention is to provide a method of treating Types I and II Herpes simplex viruses in mammals by topically administering high molecular weight fractions of antiviral lignosulfonates obtained by dialysis of or reverse osmosis on lignosulfonate solutions.

These and other objects of the present invention will become apparent to one skilled in the art from a consideration of following detailed embodiments.

The lignosulfonates useful as antiviral agents in the present invention are lignosulfonates which are obtained by sulfonation of natural lignins. The exact structure of lignosulfonates have not been completely determined, but it is known that the basic lignin monomer unit is a substituted phenylpropane. Despite the fact that lignosulfonates cannot be specified with certainty in terms of chemical formula, it has been found that a wide range of those contained in spent liquors of the sulfite pulping of hard and soft wood or combinations thereof, or those which are manufactured from wood specifically for the purpose of making a lignin sulfonate, are useful in practicing the present invention. Although calcium is the predominant cation associated with lignosulfonates in spent liquor of industry, other pharmaceutically acceptable cations such as magnesium, sodium, potassium and ammonium are sometimes the cation of choice during wood pulping. Lignosulfonates of all of the aforementioned cations besides calcium, as well as zinc and aluminum, and useful in the present invention may be obtained by action of the appropriate sulfite salt on calcium lignosulfonates.

The crude lignosulfonate liquors together with pharmaceutical accoutrements are suitable antiviral agents in the practice of this invention, and it has been demonstrated that the crude lignosulfonates even in the presence of their contained sugars are therapeutically effective in combating Herpes simplex viruses, Types I and II.

The crude lignosulfonates found to be useful in the present invention are available as concentrated solutions or in solid form usually resulting from spray drying. An example of a crude lignosulfonate demonstrated to be useful in the present invention is Orzan $A^{TM}$ manufactured by Crown Zellerbach Corp. of Camas, Washington, which is powdered ammonium lignosulfonate containing the soluble ammonium lignosulfonates plus soluble carbohydrates resulting from sulfurous acid treatment of wood chips. It contains reducing sugars in a ratio of about 21 parts by weight reducing sugars to 79 parts by weight lignosulfonates (15% reducing sugar on a total weight basis). Other lignosulfonates containing high proportions of carbohydrates and demonstrated to be suitable for use in the present invention are Orzan $S^{TM}$ and Orzon AH-$3^{TM}$. Further definition of the Orzan™ products are given by Vocac and Alphin, Arch. Intern. Pharmacodyn. 177 No. 1, pp 150–158 (1969), and still another commercial lignosulfonate containing, on a moisture-free basis, 18.5% reducing sugars is Norlig 11™ produced by American Can Co., N.Y., N.Y., detailed typical analysis for which is given in U.S. Pat. No. 4,004,002, all of which disclosures are incorporated by reference.

Among lignosulfonates refined to remove sugars are those prepared by the process of Jantzen, U.S. Pat. No. 2,838,483, which are the alkali metal Peritans™ prepared by absorption of lignosulfonates on chrome tanned hide scraps to the exclusion of sugars, the disclosure of which is incorporated by reference.

Lignosulfonates derived from sulfite wood pulping having sugars removed by the Jantzen process and demonstrated to be useful in the practice of this invention are those Peritans™ which have been commercially available in the past from Norcem of Oslo, Norway, and Arthur Trask Co. of Chicago, Ill. Typical analyses of Peritan Na™ and Peritan $NH_4$™ are given in U.S. Pat. No. 4,004,002 and they contain typically only 0.02 to 0.1% by weight reducing sugars, the disclosure of which is incorporated by reference.

Lignosulfonates in spent sulfite liquors have a wide range of molecular weight of from 250 (the assumed monomer Mol. wt.) to about 100,000 or more. We have found that when the lower molecular weight fraction of lignosulfonates, as well as the sugars, are removed an even more effective antiviral agent is obtained. These high molecular weight fractions of lignosulfonates are the preferred antiviral agents of this invention.

Among the lignosulfonates which have been refined to remove both sugars and low molecular weight lignosulfonates are the aforementioned Peritans™ which have been further subjected to dialysis or reverse osmosis to remove a portion of low molecular weight lignosulfonates or to completely remove low molecular weight lignosulfonates below a certain molecular weight level as defined by the membrane used in reverse osmosis.

The following preparations 1, 2A and 3 describe the procedures whereby the preferred high molecular weight fractions are obtained by dialysis or reverse osmosis. Preparation 2B furnishes a low molecular weight fraction of lignosulfonates which, when tested for antiviral activity against Herpes virus Type I in HEp-2 monolayers, gave a negative result.

Preparation 1

(Dialysis of Sugar-Free Lignosulfonate Solution)

A 10% solution of Peritan NA™ (prepared by the Jantzen process of U.S. Pat. No. 2,838,483 to remove sugars) in distilled water was prepared (pH 8.5) and the pH adjusted to approximately 4.0 with gaseous sulfur dioxide. The solution was transferred to a dialysis apparatus consisting of an inlet reservoir, a constant feed peristaltic pump, a 25 l. running water dialysis bath, 25 ft. of 1⅛inch Visking No. 14 cellulose dialysis tubing and a receiving container. The Peritan solution (pH 4.0) was pumped through the dialysis tubing at a rate of 4 to 6 ml. per minute. Total retention time in the dialysis tubing was 5 to 7 hours. Lignosulfonates of low molecular weight amounting to 10 to 15% of the total weight passed out in the water and were discarded. The dialyzed solution was passed through a charcoal bed (Darco granular 20×40) containing 100 g. of charcoal per kg. of starting Peritan NA. Excess water was removed on a steam heated flash evaporator to a concentration of 22 g. per 100 ml.

This solution was spray dried. Drying conditions were as follows:

| | |
|---|---|
| Feed Rate | 340 ml./min. |
| Inlet Temp. | 500° F. |
| Outlet Temp. | 295–305° F. |

The dried material contained 2% water by weight. Other analyses on a weight percentage basis are as follows:

| | |
|---|---|
| Carbon | 49.80 |
| Hydrogen | 5.52 |
| Nitrogen | <0.5 |
| Sulfur | 6.00 |
| Oxygen 33.80 | |
| Sodium 3.82 | |
| Methoxyl 15.50 | |
| Hydroxyl 0.62 | |

Preparations 2A and 2B (Fractionation on Basis of Molecular Weight By Reverse Osmosis)

Peritan NA™ prepared by the process of U.S. Patent 2,838,482 to remove sugars (Arthur C. Trask Co., Chicago, Ill.) was dissolved in water and subjected to reverse osmosis at 300 psig. using a Havens International Type 215 membrane until the perfusate concentration of lignosulfonate was less than 1 mg/ml. The Havens 215 membrane has the ability to reject 85% of an 8% concentration of PEG-20M having a molecular weight of 20,000 at a temperature of 20° C., 150 psi. pressure and a flow of 1 gal. per min. in a single pass.

(A) High Molecular Weight Fraction

The material which did not pass through the 215 membrane (retentate) was filtered and the solution spray dried to give a tan lignosulfonate powder. This fraction accounts for about one-half by weight of the initial weight of the starting Peritan NA™.

(B) Low Molecular Weight Fraction

The total perfusate was then combined and concentrated by passing it through a 310 Havens hollow core tube membrane to reduce water content, filtered and spray dried to give a tannishgray powder. This powder was dissolved in water and passed through a Dowex 50W ion-exchange column (Na+ form) to remove iron and left to dry by air evaporation to give a light tan powder when ground. The amount of product represented about one-half the starting Peritan NA™ on a weight basis. The average molecular weight determined by ultracentrifugation in 0.333 molar KCl solution was 3080. Data were analyzed by the method of Williams., J. Phys. Chem. 69, 1050 (1965).

Preparation 3

Dialysis of Sulfite Liquor

An ammonium based sulfite liquor concentrated to 40% solids was subjected to dialysis using a non-selective membrane consisting of Visking Fiberous 14 membrane material (2 mil. thickness) against treated well water to remove 46% of the low molecular weight sugars and lignin by the following equipment and procedure.

Equipment

A large commercial type dialyzer provided with a system of two 50-gallon polyethylene drums which were used as recycle tanks for the process liquor and the dialyzing water. The liquor tank was fitted with a stainless steel 316 Goulds centrifugal pump capable of pumping 30 gallons per minute at 15 psig. pressure and the water tank with two Eastern U-34F (Hostelloy C) pump each capable of pumping 16.5 gallons per minute at 15 psig. The dialyzer unit was 100 cm. × 60 cm. × 0.1 cm. having fifty liquor and fifty-one water frames. The frames were separated by sheets of Visking Fiberous 14 membrane material. The liquor and water flows were parallel through individual frames.

Procedure

At the beginning of the process period, twenty-five gallons of the sulfite liquor solution was pumped into the liquor recycle tank and from there to the liquor inlet parts at the base of the dialysis stack under 15 psig. pressure. The dialyzing water which has been treated with a Culligan unit to remove iron salts was pumped from the water recycle tank to the base of the dialysis stack and the process started with balanced pressures on both streams. Transfer of water from the dilute to the liquor side of the membrane was reduced later in the process period by maintaining a slight pressure of 1-2 psig. excess pressure on the liquor side of the membrane. After five hours of processing to establish equilibrium, the overflow in the side of the liquor recycle tank was opened and approximately two gallons of treated liquor was withdrawn and the liquor feed was initiated at a rate of 500 ml. per minute. Liquor feed rates of 500 ml. per minute of 40% liquor and water feed rates of 1-2 gallons per minute were maintained throughout the dialyzing period with the treated liquor overflow going to storage. It was established that 46% by weight of the initial solids were dialyzed out. The treated liquor was spray dried.

The lignosulfonates of the present invention are administered topically to the tissue of the host under viral attack in liquid forms such as solutions, emulsions and sprays; in solid and semi-solid forms such as suppositories, powders, jellies, ointments, creams, troches, pastilles, lozenges or any solids or semi-solids capable of releasing lignosulfonates over a period of time. When the treatment is in the mouth, sprays, mouthwashes and swabs are particularly effective means of application. Suitable liquid preparations can be prepared wherein the concentration of the lignosulfonate is 0.5 to 20.0 percent, the preferred concentration being 1.0 to 10.0 percent. The concentration of lignosulfonate in the solid preparation can also be 0.5 to 20%, the preferred concentration being 3.0 to 10.0 per cent.

VIROLOGY

Methods (a) Antiviral Test Procedures, Experimental Compounds vs. Viruses in Cell Culture.

The test system consists of monolayers of a continuous human cell line, the HEp-2 cell, infected with 30 plaque-forming units of Herpes simplex virus Type I or II and incubated for 72 hours at 35° C.

Experimental compounds are made up in tissue culture medium and applied to the cell monolayers immediately after infection at concentrations of one microgram to 1 mg. per monolayer. Activity is judged by comparing the number of plaques formed in the control monolayers with the number formed in each treated monolayer and expressing the results in percent plaque reduction. Toxic effects are judged by vital staining of the cell monolayer with neutral red stain. Active compounds are defined as those that show 50% plaque reduction without attendant toxicity in at least two compound concentration levels.

(b) Antiviral Test Procedure, Experimental Compounds vs. Genital Herpes Simplex Virus (HSV) Infection in Animals.

1. Female White Mice. The test system is composed of 5-week-old mice, rendered susceptible to HSV Type II infection by mating or hormonal induction of pseudopregnancy. Animals are infected by intravaginal instillation of a virus dose adjusted to cause disease and death in 80–100% of untreated infected control mice.

Experimental compounds at various dose levels are administered as intravaginal douches of about 0.1 ml. of 5% lignosulfonate solution at intervals before and after infection.

Activity is evaluated in terms of the "mean survival day" (MSD) for each test and control group, where the day of death of each unprotected mouse is scored, surviving animals are scored as total test days plus 1, and a comparison is made of the means of these MSD's among groups. The percent of protected animals in each group is used as a second measure of protection or activity.

2. Female Guinea Pigs. Virgin guinea pigs weighing 250 grams each constitute the test system. No special pretreatment is required to increase susceptibility to infection. Animals are infected by mildly abrading the vaginal mucosa, e.g., with a dry cottom swab, and instilling HSV Type I or II into the vagina, or by abrading the external labia gently with emery cloth and swabbing the virus onto this area. The virus dose used is adjusted to infect 80–100% of unprotected animals with resulting disease and death. Experimental compounds at various dose levels are administered as intravaginal douches at intervals before and after infection. Activity is evaluated in terms of the "mean survival days" and percent protection of treated groups are compared to sham-treated groups, as is described hereinabove for the mouse HSV model.

The following examples illustrate the lignosulfonates which are useful in the method of this invention. It is to be understood that the examples are merely illustrative of which lignosulfonates can be used and are not to be construed as limiting.

EXAMPLE 1

(Herpes Simplex Virus, Type I, in Human Cell Line).

Antiviral activity of lignosulfonates (LS) in terms of 50% plaque reduction in HEp-2 monolayers infected with Herpex simplex virus Type I was determined by method (a) above. Results are in Table 1.

Table 1

Protection Against Herpes Simplex Virus, Type I, in Hep-2 Monolayers with Lignosulfonates (LS)

| LS Tested | Active Concentrations, micrograms LS per ml. (non-toxic, 50% plaque reduction) |
|---|---|
| Peritan NH4 TM | 1000–10 |
| Peritan NA TM | 500–50 |
| Dialyzed Peritan NA TM (Preparation 1) | 1000–50 |
| High Mol. Wt. LS from Reverse Osmosis treatment of Peritan NA TM (Preparation 2A) | 1000–50 |
| Low Mol. Wt. LS from Reverse Osmosis treatment of Peritan NA TM (Preparation 2B) | negative |
| Norlig 11 TM | 1000–250 |
| Maratan 24 TM | 1000–50 |
| Orzan A TM (NH4 LS) | 1000–50 |
| Orzan AH-3 TM (NH4 LS) | 1000–50 |
| Orzan G TM (NH4 LS) | 1000–50 |
| Orzan LS TM (Na LS) | 1000–50 |
| Orzan S TM (Na LS) | 1000–50 |
| Calcium LS (SL 366000) (hardwood), Scott Paper Co. | 1000–250 |
| Calcium LS High Mol. Wt. (hardwood), Scott Paper Co. | 1000–50 |
| Dialyzed Ammonium Sulfite Liquor (Preparation 3) | 1000–50 |

Table 2

Protection Against Herpes Simplex Virus, Type II, in HEp-2 Monolayers with Lignosulfonates (LS)

| LS Tested | Active Concentrations, micrograms LS per ml. (non-toxic, 50% plaque reduction |
|---|---|
| Peritan TM | 1000–100 |
| Orzan A TM | 500–50 |
| Orzan LA TM | 250–50 |
| Orzan S TM | 500–50 |
| Calcium LS (SL-366000) | 500–100 |
| Calcium LS High Mol. Wt. (hardwood) | 1000–50 |
| Dialyzed Ammonium Sulfite Liquor (Preparation 3) | 500–50 |

EXAMPLE 3

(Herpes Simplex Type II Virus—Mice)

Antiviral activity of lignosulfonates (LS) in terms of mean survival days and percentages of mice protected against vaginal infection with Herpes simplex virus, Type II, was determined by method (b—1) above, topically applying aqueous LS solutions periodically as douches, pre- and post-infection. Results are in Table 3.

Table 3

Treatment of Herpes Simplex, Type II, Virus in Mice with Lignosulfonates (LS)

| LS Tested | Dosage Regimen (Douche) | | Results | |
|---|---|---|---|---|
| | Conc. LS in Aqueous Solution wt. % | Timing of Douche | Mean Survival Days | Percent Protection |
| Dialyzed Peritan NA TM (Preparation 1) | 5 | (a)Pre & Post infection | 13.7 | 86 |
| High Mol. Wt. LS from Reverse Osmosis (Preparation 2A) | 5 | (a)Pre & Post infection | 13.6 | 71 |
| Orzan AH-3 TM | 5 | (a)Pre & Post infection | 11.6 | 50 |
| Control (water only) | 5 | (a)Pre & Post infection | 7.6 | 0 |
| Dialyzed Ammonium Sulfite LIquor (Preparation 3) | 5 | (b)Pre & Post infection | 15.0 | 100 |
| Dialyzed Ammonium Sulfite Liquor (Preparation 3) | 10 | (b)Pre & Post infection | 15.0 | 100 |
| Dialyzed Ammonium Sulfite Liquor (Preparation 3) | 10 | (b)Pre & Post infection | 15.0 | 100 |
| Control (water only) | — | (b)Pre & Post infection | 9.0 | 10 |

(a)Douches 2–3 hr. prior to and following infection; twice daily days 2–4; once on 5th day.
(b)Douches 3 hrs. prior to infection and 3 hrs. post infection and twice daily for 4 days.

EXAMPLE 2

(Herpes Simplex Virus, Type II, in Human Cell Line)

Antiviral activity of lignosulfonates (LS) in terms of 50% plaque reduction in HEp-2 monolayers infected with Herpes simplex virus Type II was determined by method (a) above. Results are in Table 2

EXAMPLE 4

(Herpes Simplex Type I Virus—Guinea Pigs)

Antiviral activity, in terms of mean-survival days and percentages of guinea pigs protected against vaginal infection with Herpes simplex viruses Type I and II separately, was determined by method (b-2) above, topically applying aqueous lignosulfonate (LS) periodically as douches, pre and post infection. Results for Type I are in Table 4 and for Type II in Table 5.

Table 4
Treatment of Herpes Simplex, Type I, Virus in Guinea Pigs with Lignosulfonates (LS)

| | Dosage Regimen (Douche) | | Results | |
|---|---|---|---|---|
| LS Tested | Conc. LS in Aq. Buffer[a] Solution Wt. % | Timing of Douche | Mean Survival Days | Percent Protection |
| Dialyzed Peritan NA ™ (Preparation 1) | 5 | [b]Pre & Post infection | 10.6 | 50 |
| Control (Aq. Buffer)[a] | — | [b]Pre & Post infection | 5.3 | 0 |

[a]Phosphate buffer, pH = 7.
[b]Douches 30 min. prior to infection and 4 hrs. post infection; four times daily days 1 and 2 and twice daily days 3 and 4.

Table 5
Treatment of Herpex Simplex, Type II, Virus in Guinea Pigs with Lignosulfonates (LS)

| | Dosage Regimen (Douche) | | Results | |
|---|---|---|---|---|
| LS Tested | Conc. LS in Aq. Buffer Solution[a] Wt. % | Timing of Douche | Mean Survival Days | Percent Protection |
| Dialyzed Peritan NA ™ (Preparation 1) | 5 | [b]Pre & Post infection | 13.0 | 75 |
| Control (Aq. Buffer)[a] | — | [b]Pre & Post infection | 7.0 | 0 |
| Dialyzed Ammonium Sulfite Liquor (Preparation 3) | 5 | [c]Pre & Post infection | 11.1 | 50 |
| Control (Aq. Buffer)[a] | — | [c]Pre & Post infection | 6.3 | 0 |

[a]Phosphate buffer, pH=7.
[b]Douches 30 min. prior to infection, 30 min. post infection and 4 hrs. post infection; four times daily days 1 to 4.
[c]Douches 1 hr. prior to and following infection, and 4 hrs. post infection; twice daily days 1 to 4.

Formulation and Administration

Effective quantities of antiviral lignosulfonates may be administered topically to the tissue of a living animal body under attack by the Herpes simplex virus in any one of various ways depending on the site of infection. When the oral cavity is involved, liquid preparations to be used as mouthwashes or swabs are ideal vehicles for carrying the lignosulfonates. Such suitable liquid preparations may contain 0.5 to 20.0% lignosulfonates. When the genital area is involved, powders, solutions, emulsions, jellies, ointments and suppositories may be used within these same concentration ranges. Ideally, the tissues under attack are treated 2–4 times daily.

The active agents of the invention may be combined with other pharmacologically active agents, buffers and antacids or the like for administration.

Examples of compositions within the ranges given are as follows and are representative for all of the pharmacologically active lignosulfonates of the invention but have been especially designed to embody as active ingredient the lignosulfonates which have been purified as described hereinabove.

MOUTH WASH

| | Solution Formulations Percent Lignosulfonates | |
|---|---|---|
| Ingredients | 5% | 10% |
| 1. Lignosulfonate | 50.0 gm. | 100.0 gm. |
| 2. Sarbo | 150.0 ml. | 150.0 ml. |
| 3. Glycerin | 100.0 ml | 100.0 ml. |
| 4. Sodium Benzoate | 1.0 gm. | 1.0 gm. |
| 5. Sucrose | 40.0 gm. | 50.0 gm. |
| 6. 0.2N Hcl | 100.0 gm. | 140.0 ml. |
| 7. Peppermint Flavor Compound No. 21444 Fritzsche | 0.35 ml. | 0.75 ml. |
| 8. Oil of Spearmint N.F., Fritzsche | 0.5 ml. | 0.75 ml. |
| 9. Alcohol, U.S.P. 95% | 50.0 | 50.0 ml. |
| 10. Caramel Color Acid-proof | 6.0 | — |
| 11. Water U.S.P., q.s. | 1000.0 ml. | 1000.0 ml. |

Procedure

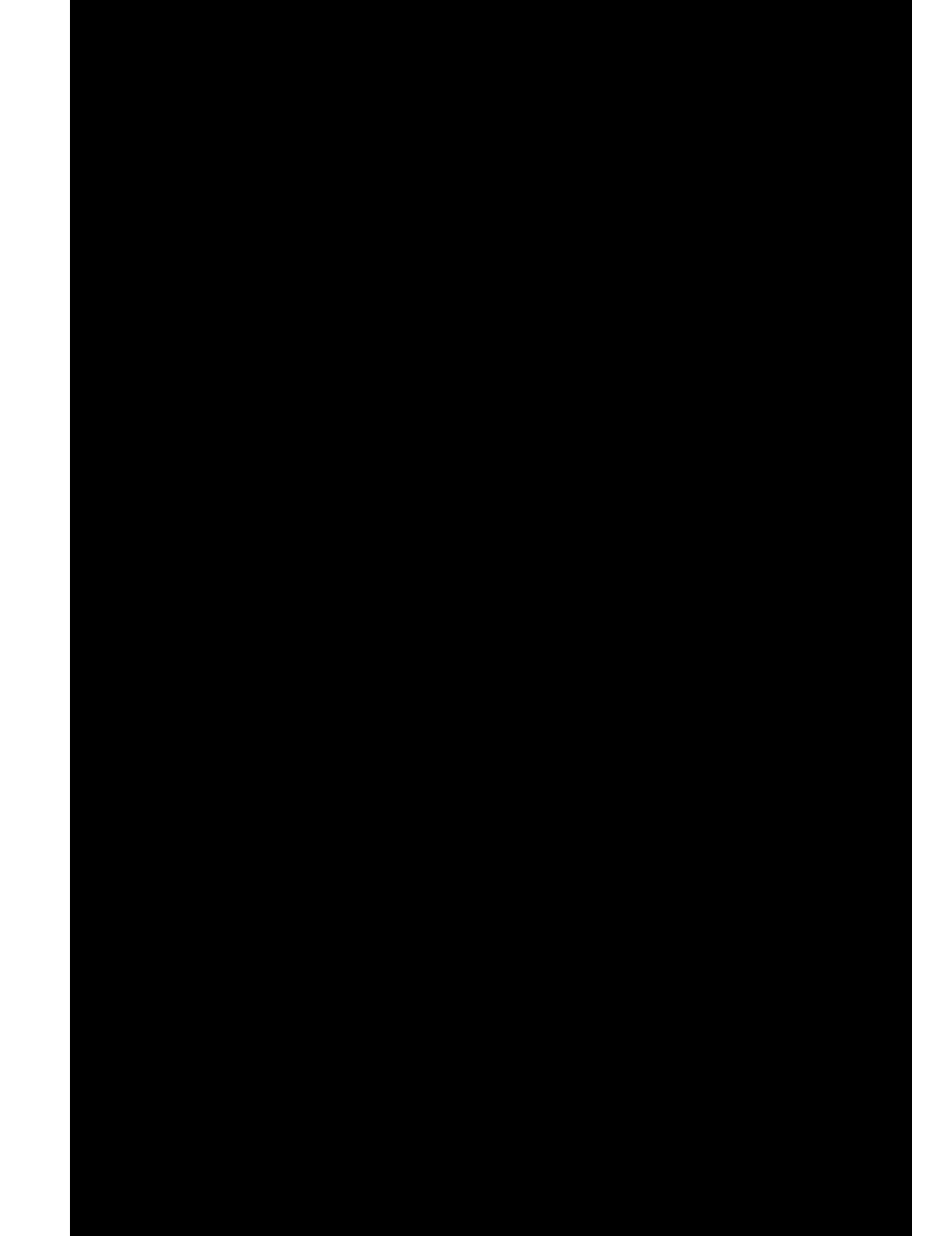

1. Dissolve the sodium benzoate in 350 ml. of water.
2. Mix lignosulfonate and sucrose and add this to the mixing solution from step No. 1.
3. After step No. 2 is a solution, add the glycerin and sorbo.
4. Put the flavors in part of the alcohol and add this to the solution. Rinse the container with the remainder of the alcohol and add to batch.
5. Adjust pH to 3.0 to 3.5 using 0.2 N Hcl.
6. Add caramel.
7. Q.S. to final volume with water.